(12) United States Patent
Tsusaki et al.

(10) Patent No.: US 6,383,769 B1
(45) Date of Patent: *May 7, 2002

(54) POLYPEPTIDES HAVING β-FRUCTOFURANOSIDASE ACTIVITY

(75) Inventors: Keiji Tsusaki; Michio Kubota; Hiroto Chaen, all of Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/317,179

(22) Filed: May 24, 1999

Related U.S. Application Data

(62) Division of application No. 08/870,827, filed on Jun. 6, 1997, now Pat. No. 5,962,297.

(30) Foreign Application Priority Data

Jun. 10, 1996 (JP) ............................................... 8-170620

(51) Int. Cl.[7] .............................. C12Q 1/48; C12N 9/24
(52) U.S. Cl. ........................................ 435/15; 435/200
(58) Field of Search .................................... 435/15, 200

(56) References Cited

U.S. PATENT DOCUMENTS

| | | | |
|---|---|---|---|
| 4,487,198 A | | 12/1984 | Miyake et al. |
| 4,521,252 A | | 6/1985 | Miyake et al. |
| 5,753,469 A | * | 5/1998 | Nakada et al. ................ 435/99 |
| 5,952,204 A | * | 9/1999 | Nakada et al. ................ 435/99 |

FOREIGN PATENT DOCUMENTS

| | | | |
|---|---|---|---|
| EP | 0780470 | | 6/1997 |
| JP | 05276970 | * | 10/1993 |

OTHER PUBLICATIONS

Akamatsu et al, "Transformation of Bacillus Protoplasts by Plasmid pTP4 DNA", *Agric. Biol. Chem.* 1617–1621 (1982).

Chambert et al, "Levansucrae of Bacillus subtillis", *Eur. J. Biochem.* 71:493–508 (1976).

Gay et al, "Cloning Structural Gene sac3, Which Codes for Exoenzyme Levansucrase of Baccillus Subtilis: Expression of the Gene in Escherichia coli", *J. Bacteriol.* 153(3):1424–1431 (1983).

Lepesant et al, "Identification of the Structural Gene of Levansucrase in Bacillus subtilis Marburg", *Molec. Gen. Genet.* 128:213–221 (1974).

Sambrook et al, *Molecular Cloning: A Laboratory Manual*, 2nd Ed., Cold Spring Harbor Laboratory Press (1989).

Schaeffer et al, "Fusion of bacterial protoplasts", *Proc. Natl. Acad. Sci. USA* 73(6):2151–2155 (1976).

Steinmetz et all, "The DNA sequence of the gene for the secreted Bacillus subtilis enzyme levansucrase and its genetic control sites", *Mol. Gen. Genet.* 200;220–228 (1985).

XP–002105460, Database WPI, Section Ch, Week 9235, Derwent Publications Ltd., London, GB; Class B04, AN 92–290152 & JP 04 200386 A (NISSHIN SEITO KK), Jul. 21, 1992 Abstract.

XP–002105461, Database WPI, Section Ch, Week 8702, Derwent Publications Ltd., London, GB; Class B03, AN 87–010765 & JP 61 268191 A (SHUNGIJUTSU KAIHATSU KK), Nov. 27, 1986 Abstract.

XP–002105578, Database WPI, Section Ch, Week 8705, Derwent Publications Ltd., London, GB; Class D16, AN 87–031700 & JP 61 268179 A (SHINGIJUTSU KAIHATSU KK), Nov. 27, 1986 Abstract.

* cited by examiner

*Primary Examiner*—Ponnathapu Achutamurthy
*Assistant Examiner*—Peter P. Tung
(74) *Attorney, Agent, or Firm*—Browdy and Neimark

(57) ABSTRACT

Disclosed are a polypeptide having a β-fructofuranosidase activity obtainable by the expression of a microbial gene, a DNA encoding the polypeptide, a transformant obtained by introducing the DNA into an appropriate host, a process for producing the polypeptide comprising culturing the transformant to produce the polypeptide and collecting the produced polypeptide from the culture, and a method for fructofuranosyl transfer comprising a step of reacting a fructofuranosyl donor with a fructofuranosyl acceptor in the presence of the polypeptide.

5 Claims, 6 Drawing Sheets

- ; Acetate buffer
▲ ; Tris-HCl buffer
○ ; Acetate buffer with 5 mM calcium chloride
△ ; Tris-HCl buffer with 5 mM calcium chloride

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 21 amino acids
      (B) TYPE: amino acid
      (D) TOPOLOGY: linear (v) FRAGMENT TYPE: N-terminal fragment (xi) SEQUENCE DESCRIPTION: SEQ ID NO: 1:

Met Asn Ser Gly Asp Tyr Lys Glu Asp Tyr G ly Phe Ala His Ile Thr
1           5                  10                15

Arg Ala Asp Met Leu
          20

(2) INFORMATION FOR SEQ ID NO: 2:

(i) SEQUENCE CHARACTERISTICS:

(A) LENGTH: 12 amino acids
        (B) TYPE: amino acid
        (D) TOPOLOGY: linear (v) FRAGMENT TYPE: internal fragment (xi) SEQUENCE DESCRIPTION: SEQ ID NO: 2:

Ser Val Phe Asp Gly Gly Asp Gly Thr Val Tyr Gln
1               5                   10

(2) INFORMATION FOR SEQ ID NO: 3:

(i) SEQUENCE CHARACTERISTICS:
        (A) LENGTH: 455 amino acids
        (B) TYPE: amino acid
        (D) TOPOLOGY: linear (ii) MOLECULE TYPE: peptide (xi) SEQUENCE DESCRIPTION: SEQ ID NO: 3:

Met Asn Ser Gly Asp Tyr Lys Glu Asp Tyr Gly Phe Ala His Ile Thr
1               5                   10                  15

Arg Ala Asp Met Leu Lys Ile Pro Gly Gln Gln Asn Ser Pro Gln Phe
                20                  25                  30

Lys Val Pro Gln Phe Asn Ala Ser Ala Ile Lys Asn Ile Asp Ser Ala
            35                  40                  45

Lys Gly Tyr Asp Lys Ser Gly Asn Leu Ile Asp Leu Asp Val Trp Asp
50                  55                  60

Ser Trp Pro Leu Gln Asn Ala Asp Gly Thr Ala Ala Asn Tyr His Gly
65                  70                  75                  80

Tyr His Ile Val Ser Ala Leu Ala Gly Asp Pro Lys Asn Ser Asp Asp
                85                  90                  95

Thr Pro Leu His Leu Phe Tyr Gln Lys Val Gly Asp Thr Ser Ile Asp
                100                 105                 110

Ser Trp Lys Asn Ala Gly Arg Val Phe Glu Asp Met Asp Lys Phe Val
            115                 120                 125

Pro Asn Asp Pro Tyr Leu Lys Tyr Gln Thr Gln Glu Trp Ser Gly Ser
130                 135                 140

Ala Thr Leu Thr Lys Asp Gly Gln Val Arg Leu Phe Tyr Thr Asp Tyr
145                 150                 155                 160

Ser Gly Asn Pro Glu Asp Gly Gly Thr Gly Ala Gly Asn Gln Ile Ile
                165                 170                 175

Ser Thr Ala Gln Val Asn Leu Ser Gln Pro Asp Ala Ala Thr Leu Lys
            180                 185                 190

Val Asp Gly Val Ser Asp His Lys Ser Val Phe Asp Gly Gly Asp Gly
        195                 200                 205

Thr Val Tyr Gln Asn Ile Gln Gln Phe Ile Asp Glu Gly Lys Trp Ile
210                 215                 220

Ser Gly Asp Asn His Thr Leu Arg Asp Pro His Tyr Val Glu Asp Lys
225                 230                 235                 240

Gly His Lys Tyr Leu Val Phe Glu Ala Asn Thr Gly Thr Thr Asp Gly
                245                 250                 255

Tyr Gln Gly Asp Gln Ser Phe Asn Asn Lys Ala Tyr Tyr Gly Gly Ser
            260                 265                 270

Asp Val Phe Phe Gln Asn Glu Lys Asn Lys Leu Leu Gln Ser Pro Lys
        275                 280                 285

Lys Gln Ile Ala Ser Leu Ala Asn Gly Ala Leu Gly Ile Val Glu Leu
290                 295                 300

```
Ala Asp Asp Tyr Thr Val Lys Ser Val Met L ys Pro Leu Val Ala Ser
305                 310                 315                 320

Asn Thr Val Ala Asp Glu Val Glu Arg Ala A sn Ile Phe Lys Met Asn
            325                 330                 335

Asn Lys Trp Tyr Leu Phe Thr Asp Ser Arg G ly Ser Lys Met Thr Ser
            340                 345                 350

Asp Gly Ile Asn Asp Lys Asp Val Tyr Met L eu Gly Pro Gly Gly Asp
            355                 360                 365

Ser Leu Asn Gly Pro His Asn Pro Ile Asn G lu Thr Gly Leu Val Leu
    370                 375                 380

Asn Met Asn Leu Asp Pro Ala Asp Leu Thr H is Thr Tyr Ser His Cys
385                 390                 395                 400

Gly Ile Pro His Pro Glu Gly Asn Asn Val V al Leu Thr Ser Tyr Met
            405                 410                 415

Thr Asn Arg Gly Phe Tyr Pro Glu His His S er His Leu Arg Asp Lys
            420                 425                 430

Leu Gly Val Asn Ile Lys Gly Ser Asp Thr S er Gly Gly Glu Asn Ser
            435                 440                 445

Ser Gly Gln Gly Gln Phe Pro
    450                 455

(2) INFORMATION FOR SEQ ID NO: 4:

(i) SEQUENCE CHARACTERISTICS:
        (A) LENGTH: 1365 base pairs
        (B) TYPE: nucleic acid
        (C) STRANDEDNESS: double
        (D) TOPOLOGY: linear (xi) SEQUENCE DESCRIPTION: SEQ ID NO: 4:

ATG AAC AGC GGG GAC TAC AAG GAA GAC TAT G GT TTT GCC CAT ATT ACA        48
Met Asn Ser Gly Asp Tyr Lys Glu Asp Tyr G ly Phe Ala His Ile Thr
1               5                   10                  15

CGC GCT GAC ATG CTA AAA ATT CCA GGA CAA C AA AAC AGT CCT CAA TTT        96
Arg Ala Asp Met Leu Lys Ile Pro Gly Gln G ln Asn Ser Pro Gln Phe
            20                  25                  30

AAA GTG CCT CAA TTC AAT GCA TCA GCA ATC A AA AAC ATT GAT TCG GCA       144
Lys Val Pro Gln Phe Asn Ala Ser Ala Ile L ys Asn Ile Asp Ser Ala
        35                  40                  45

AAA GGG TAT GAT AAG TCA GGC AAC TTA ATA G AT TTA GAT GTA TGG GAT       192
Lys Gly Tyr Asp Lys Ser Gly Asn Leu Ile A sp Leu Asp Val Trp Asp
    50                  55                  60

AGC TGG CCA CTG CAA AAC GCT GAT GGT ACT G CG GCA AAT TAT CAT GGA       240
Ser Trp Pro Leu Gln Asn Ala Asp Gly Thr A la Ala Asn Tyr His Gly
65              70                  75                  80

TAT CAC ATC GTC TCC GCT TTA GCA GGT GAC C CA AAA AAC AGT GAT GAT       288
Tyr His Ile Val Ser Ala Leu Ala Gly Asp P ro Lys Asn Ser Asp Asp
            85                  90                  95

ACT CCA CTT CAT TTA TTC TAT CAA AAA GTC G GT GAT ACA TCG ATT GAC       336
Thr Pro Leu His Leu Phe Tyr Gln Lys Val G ly Asp Thr Ser Ile Asp
100                 105                 110                 115

AGC TGG AAA AAT GCT GGA AGA GTA TTT GAA G AT ATG GAT AAA TTT GTT       384
Ser Trp Lys Asn Ala Gly Arg Val Phe Glu A sp Met Asp Lys Phe Val
            120                 125                 130

CCA AAT GAT CCG TAT CTT AAA TAT CAA ACA C AG GAG TGG TCA GGT TCT       432
Pro Asn Asp Pro Tyr Leu Lys Tyr Gln Thr G ln Glu Trp Ser Gly Ser
            135                 140                 145

GCT ACT TTA ACC AAA GAT GGC CAA GTC CGT T TA TTC TAT ACA GAT TAC       480
```

```
                                                                                          -continued Ala Thr Leu Thr Lys Asp Gly Gln Val Arg L eu Phe Tyr Thr Asp Tyr
        150                 155             160

TCA GGT AAT CCT GAA GAT GGT GGA ACC GGT G CT GGT AAC CAA ATC ATT              528
Ser Gly Asn Pro Glu Asp Gly Gly Thr Gly A la Gly Asn Gln Ile Ile
    165                 170             175

TCA ACT GCT CAA GTA AAC TTA TCC CAG CCG G AT GCA GCT ACA CTT AAA              576
Ser Thr Ala Gln Val Asn Leu Ser Gln Pro A sp Ala Ala Thr Leu Lys
180             185                 190                 195

GTC GAT GGA GTA TCT GAT CAT AAA TCT GTC T TT GAT GGC GGA GAC GGT              624
Val Asp Gly Val Ser Asp His Lys Ser Val P he Asp Gly Gly Asp Gly
                200             205             210

ACA GTT TAT CAA AAT ATT CAG CAA TTT ATC G AT GAA GGC AAG TGG ATT              672
Thr Val Tyr Gln Asn Ile Gln Gln Phe Ile A sp Glu Gly Lys Trp Ile
            215                 220             225

TCA GGT GAT AAC CAT ACT TTA AGA GAC CCT C AC TAT GTT GAA GAT AAG              720
Ser Gly Asp Asn His Thr Leu Arg Asp Pro H is Tyr Val Glu Asp Lys
        230                 235             240

GGC CAT AAA TAT CTT GTC TTT GAA GCG AAT A CT GGA ACA ACA GAT GGT              768
Gly His Lys Tyr Leu Val Phe Glu Ala Asn T hr Gly Thr Thr Asp Gly
    245                 250             255

TAT CAA GGC GAT CAG TCT TTC AAT AAT AAA G CT TAC TAT GGC GGA AGT              816
Tyr Gln Gly Asp Gln Ser Phe Asn Asn Lys A la Tyr Tyr Gly Gly Ser
260             265                 270                 275

GAC GTC TTC TTC CAG AAT GAA AAA AAT AAA C TG CTT CAA AGT CCT AAA              864
Asp Val Phe Phe Gln Asn Glu Lys Asn Lys L eu Leu Gln Ser Pro Lys
                280             285             290

AAA CAA ATT GCT TCT TTA GCG AAT GGT GCA T TA GGC ATT GTT GAA TTG              912
Lys Gln Ile Ala Ser Leu Ala Asn Gly Ala L eu Gly Ile Val Glu Leu
            295                 300             305

GCC GAT GAC TAT ACA GTG AAA AGT GTT ATG A AA CCA TTA GTC GCA TCA              960
Ala Asp Asp Tyr Thr Val Lys Ser Val Met L ys Pro Leu Val Ala Ser
        310                 315             320

AAC ACA GTA GCA GAT GAA GTC GAA CGC GCC A AT ATA TTT AAA ATG AAT             1008
Asn Thr Val Ala Asp Glu Val Glu Arg Ala A sn Ile Phe Lys Met Asn
    325                 330             335

AAT AAA TGG TAT CTA TTC ACG GAT TCA AGA G GA TCC AAA ATG ACG AGT             1056
Asn Lys Trp Tyr Leu Phe Thr Asp Ser Arg G ly Ser Lys Met Thr Ser
340             345                 350                 355

GAT GGA ATT AAC GAC AAA GAT GTT TAT ATG C TA GGG CCC GGA GGC GAC             1104
Asp Gly Ile Asn Asp Lys Asp Val Tyr Met L eu Gly Pro Gly Gly Asp
                360             365             370

TCC TTA AAT GGC CCA CAC AAC CCG ATA AAT G AA ACT GGA CTT GTA TTG             1152
Ser Leu Asn Gly Pro His Asn Pro Ile Asn G lu Thr Gly Leu Val Leu
            375                 380             385

AAC ATG AAT CTT GAC CCT GCT GAT CTC ACA C AC ACT TAC TCT CAT TGC             1200
Asn Met Asn Leu Asp Pro Ala Asp Leu Thr H is Thr Tyr Ser His Cys
        390                 395             400

GGT ATC CCG CAC CCT GAA GGT AAT AAT GTG G TA CTC ACA AGT TAT ATG             1248
Gly Ile Pro His Pro Glu Gly Asn Asn Val V al Leu Thr Ser Tyr Met
    405                 410             415

ACG AAT AGA GGC TTC TAT CCA GAA CAT CAC T CT CAC CTG CGG GAC AAG             1296
Thr Asn Arg Gly Phe Tyr Pro Glu His His S er His Leu Arg Asp Lys
420             425                 430                 435

CTT GGG GTT AAT ATT AAA GGG TCT GAC ACA T CT GGA GGA GAA AAT AGT             1344
Leu Gly Val Asn Ile Lys Gly Ser Asp Thr S er Gly Gly Glu Asn Ser
                440             445             450

TCC GGA CAA GGA CAA TTC CCA                                                  1365
Ser Gly Gln Gly Gln Phe Pro
            455
```

(2) INFORMATION FOR SEQ ID NO: 5:

(i) SEQUENCE CHARACTERISTICS:
        (A) LENGTH: 2408 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Bacillus sp.
        (C) INDIVIDUAL ISOLATE: V230 (FERM BP-5054)

(ix) FEATURE:
        (A) NAME/KEY: 5'UTR
        (B) LOCATION: 1..360
        (C) IDENTIFICATION METHOD : E (A) NAME/KEY: signal p eptide
        (B) LOCATION: 361..456
        (C) IDENTIFICATION METHOD : S (A) NAME/KEY: mat pept ide
        (B) LOCATION: 457..1821
        (C) IDENTIFICATION METHOD : S (A) NAME/KEY: 3'UTR
        (B) LOCATION: 1822..2408
        (C) IDENTIFICATION METHOD : E (xi) SEQUENCE DESCRIPTION: SEQ ID NO: 5:

```
CGGGGAAAAT ACTAGATTCC AATTGGCCAG ACTTCCCAGT TGGTGTAAGA G AAGAGTTCG        60

GACTGCCAAT GCAGCTGTGC GTAAGAAAAC AGCTTACTCA TGAGCAATTA C TAGAAGAAT       120

TTCAAAAGTC CTGGGATAAG GCCAAGTCCA CTTTGAAATA AACTTTTCAG C CTCTGTGTG       180

GGGGCTTTTT TGTTTTTATT TATTTCAACT GCAAGTGGTC CATCCCCTAT A TCAATTTAA       240

GACGAAATTC TAATCAATCC ATGCCATCCC CAATAAACTC GTCCTCCTCT A TACTTTTAA       300

TTAATAAGAA ACTATCAAGA GCTTTCTTAT CAAATTCATA CATATCCAAG G AGGGAGACG       360

ATG AAC TTC AAA AGA TTG GCG AAA AAA GCA G CT GCC GTA ACC TTC AGG        408
Met Asn Phe Lys Arg Leu Ala Lys Lys Ala A la Ala Val Thr Phe Arg
         -30                 -25                 -20

ACT GCT ATA TTA GTA GGA GCG GAC GGA CCG C AT ATT TTT GCG CAG CAA        456
Thr Ala Ile Leu Val Gly Ala Asp Gly Pro H is Ile Phe Ala Gln Gln
     -15                 -10                 -5

ATG AAC AGC GGG GAC TAC AAG GAA GAC TAT G GT TTT GCC CAT ATT ACA        504
Met Asn Ser Gly Asp Tyr Lys Glu Asp Tyr G ly Phe Ala His Ile Thr
1                5                  10                  15

CGC GCT GAC ATG CTA AAA ATT CCA GGA CAA C AA AAC AGT CCT CAA TTT        552
Arg Ala Asp Met Leu Lys Ile Pro Gly Gln G ln Asn Ser Pro Gln Phe
         20                  25                  30

AAA GTG CCT CAA TTC AAT GCA TCA GCA ATC A AA AAC ATT GAT TCG GCA        600
Lys Val Pro Gln Phe Asn Ala Ser Ala Ile L ys Asn Ile Asp Ser Ala
         35                  40                  45

AAA GGG TAT GAT AAG TCA GGC AAC TTA ATA G AT TTA GAT GTA TGG GAT        648
Lys Gly Tyr Asp Lys Ser Gly Asn Leu Ile A sp Leu Asp Val Trp Asp
     50                  55                  60

AGC TGG CCA CTG CAA AAC GCT GAT GGT ACT G CG GCA AAT TAT CAT GGA        696
Ser Trp Pro Leu Gln Asn Ala Asp Gly Thr A la Ala Asn Tyr His Gly
65                  70                  75                  80

TAT CAC ATC GTC TCC GCT TTA GCA GGT GAC C CA AAA AAC AGT GAT GAT        744
Tyr His Ile Val Ser Ala Leu Ala Gly Asp P ro Lys Asn Ser Asp Asp
             85                  90                  95

ACT CCA CTT CAT TTA TTC TAT CAA AAA GTC G GT GAT ACA TCG ATT GAC        792
```

-continued

```
          Thr Pro Leu His Leu Phe Tyr Gln Lys Val G ly Asp Thr Ser Ile Asp
                      100                 105               110

AGC TGG AAA AAT GCT GGA AGA GTA TTT GAA G AT ATG GAT AAA TTT GTT          840
Ser Trp Lys Asn Ala Gly Arg Val Phe Glu A sp Met Asp Lys Phe Val
            115                 120                 125

CCA AAT GAT CCG TAT CTT AAA TAT CAA ACA C AG GAG TGG TCA GGT TCT          888
Pro Asn Asp Pro Tyr Leu Lys Tyr Gln Thr G ln Glu Trp Ser Gly Ser
            130                 135                 140

GCT ACT TTA ACC AAA GAT GGC CAA GTC CGT T TA TTC TAT ACA GAT TAC          936
Ala Thr Leu Thr Lys Asp Gly Gln Val Arg L eu Phe Tyr Thr Asp Tyr
145                 150                 155                 160

TCA GGT AAT CCT GAA GAT GGT GGA ACC GGT G CT GGT AAC CAA ATC ATT          984
Ser Gly Asn Pro Glu Asp Gly Gly Thr Gly A la Gly Asn Gln Ile Ile
                165                 170                 175

TCA ACT GCT CAA GTA AAC TTA TCC CAG CCG G AT GCA GCT ACA CTT AAA         1032
Ser Thr Ala Gln Val Asn Leu Ser Gln Pro A sp Ala Ala Thr Leu Lys
                180                 185                 190

GTC GAT GGA GTA TCT GAT CAT AAA TCT GTC T TT GAT GGC GGA GAC GGT         1080
Val Asp Gly Val Ser Asp His Lys Ser Val P he Asp Gly Gly Asp Gly
                195                 200                 205

ACA GTT TAT CAA AAT ATT CAG CAA TTT ATC G AT GAA GGC AAG TGG ATT         1128
Thr Val Tyr Gln Asn Ile Gln Gln Phe Ile A sp Glu Gly Lys Trp Ile
            210                 215                 220

TCA GGT GAT AAC CAT ACT TTA AGA GAC CCT C AC TAT GTT GAA GAT AAG         1176
Ser Gly Asp Asn His Thr Leu Arg Asp Pro H is Tyr Val Glu Asp Lys
225                 230                 235                 240

GGC CAT AAA TAT CTT GTC TTT GAA GCG AAT A CT GGA ACA ACA GAT GGT         1224
Gly His Lys Tyr Leu Val Phe Glu Ala Asn T hr Gly Thr Thr Asp Gly
                245                 250                 255

TAT CAA GGC GAT CAG TCT TTC AAT AAT AAA G CT TAC TAT GGC GGA AGT         1272
Tyr Gln Gly Asp Gln Ser Phe Asn Asn Lys A la Tyr Tyr Gly Gly Ser
            260                 265                 270

GAC GTC TTC TTC CAG AAT GAA AAA AAT AAA C TG CTT CAA AGT CCT AAA         1320
Asp Val Phe Phe Gln Asn Glu Lys Asn Lys L eu Leu Gln Ser Pro Lys
            275                 280                 285

AAA CAA ATT GCT TCT TTA GCG AAT GGT GCA T TA GGC ATT GTT GAA TTG         1368
Lys Gln Ile Ala Ser Leu Ala Asn Gly Ala L eu Gly Ile Val Glu Leu
            290                 295                 300

GCC GAT GAC TAT ACA GTG AAA AGT GTT ATG A AA CCA TTA GTC GCA TCA         1416
Ala Asp Asp Tyr Thr Val Lys Ser Val Met L ys Pro Leu Val Ala Ser
305                 310                 315                 320

AAC ACA GTA GCA GAT GAA GTC GAA CGC GCC A AT ATA TTT AAA ATG AAT         1464
Asn Thr Val Ala Asp Glu Val Glu Arg Ala A sn Ile Phe Lys Met Asn
                325                 330                 335

AAT AAA TGG TAT CTA TTC ACG GAT TCA AGA G GA TCC AAA ATG ACG AGT         1512
Asn Lys Trp Tyr Leu Phe Thr Asp Ser Arg G ly Ser Lys Met Thr Ser
            340                 345                 350

GAT GGA ATT AAC GAC AAA GAT GTT TAT ATG C TA GGG CCC GGA GGC GAC         1560
Asp Gly Ile Asn Asp Lys Asp Val Tyr Met L eu Gly Pro Gly Gly Asp
            355                 360                 365

TCC TTA AAT GGC CCA CAC AAC CCG ATA AAT G AA ACT GGA CTT GTA TTG         1608
Ser Leu Asn Gly Pro His Asn Pro Ile Asn G lu Thr Gly Leu Val Leu
            370                 375                 380

AAC ATG AAT CTT GAC CCT GCT GAT CTC ACA C AC ACT TAC TCT CAT TGC         1656
Asn Met Asn Leu Asp Pro Ala Asp Leu Thr H is Thr Tyr Ser His Cys
385                 390                 395                 400

GGT ATC CCG CAC CCT GAA GGT AAT AAT GTG G TA CTC ACA AGT TAT ATG         1704
Gly Ile Pro His Pro Glu Gly Asn Asn Val V al Leu Thr Ser Tyr Met
                405                 410                 415
```

-continued

```
ACG AAT AGA GGC TTC TAT CCA GAA CAT CAC T CT CAC CTG CGG GAC AAG      1752
Thr Asn Arg Gly Phe Tyr Pro Glu His His S er His Leu Arg Asp Lys
              420                 425              430

CTT GGG GTT AAT ATT AAA GGG TCT GAC ACA T CT GGA GGA GAA AAT AGT      1800
Leu Gly Val Asn Ile Lys Gly Ser Asp Thr S er Gly Gly Glu Asn Ser
              435                 440              445

TCC GGA CAA GGA CAA TTC CCA TA GCGATTATCT CC CAATAAAA AGAAATGTCA      1853
Ser Gly Gln Gly Gln Phe Pro
              450             455

CTGGCAAGAT CCTACCTTTT CCCCAACCTT TTTTTTTAAA ATAAAGGGTT T TGTACCACC    1913

TTTAGAAGAA AAAAGAATCC TTGGCCCGGG CCAATTACCC ATTGCCGAAG G AGCTACCCA    1973

ATAAAAAAGA AATTTTCCCT TTTTAGGGGG GGAGTCCTTT TTTTCTATCT T GGGGTGGGG    2033

ATTGTTGGCC CCCACCAGGG GACCTTTATT AATTTATAGC ATGAATCTGG C GATTTTGCC    2093

TGGCCTACTT ATTATCCAAG CCGCCCAGCC AAAAATATTA AACCAAGGAA T CCTAAGAGT    2153

AGGCGGTACA GTTTACCAAC ACCTGCTGGA GGGGATGGAT ATCGCCCTCA A TACCACTTT    2213

TCTGTTCCCG ACAAATGGAA AAATGATCCG CAGAGGCCCA TCTTTTTTGG G GGAAGTATC    2273

ATTACTATTA CCTTTACAAC AAAGACTATC CAGATGGAAA TGGTACGGAA T GGCGGCATG    2333

CAACGTCCGA AGATTTATTG CATTGGACGG ACGAAGGGAT TGCCATCCCG A AGTATACCA    2393

ATAAAAATGG TGATC                                                     2408

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

GAYTAYAARG ARGAYTAYGG NTTYGC                                         26
```

POLYPEPTIDES HAVING β-FRUCTOFURANOSIDASE ACTIVITY

Cross-Reference to Related Applications

This application is a divisional application of application Ser. No. 08/870,827, filed Jun. 6, 1997, now U.S. Pat. No. 5,952,297, the entire contents of which are hereby incorporated by reference.

BACKGROUND OF THE INVENTION

1. Field of the Invention

The present invention relates to a polypeptide having an enzymatic activity, more particularly, to a polypeptide having a β-fructofuranosidase activity obtainable by the expression of a microbial gene.

2. Description of the Prior Art Fructofuranosyl-transferred saccharides such as xylosylfructoside and lactosucrose, which have strong anticariogenic activities and growth promoting activities for bifid bacteria, are highlighted as the latest sweeteners substitutable for sucrose in the food and pharmaceutical industries. The fructofuranosyl-transferred saccharides are usually produced using β-fructofuranosidases by contacting the enzymes with sucrose and amylaceous saccharides or lactose as materials. β-Fructofuranosidases derived from microorganisms of the genera Bacillus and Arthrobacter have been widely used. However, the enzyme productivity of these microorganisms is relatively low, resulting in the requirement of a considerably large-scale culture of the microorganisms as a disadvantage.

The recent progress of recombinant DNA technology is outstanding. Even an enzyme, whose total amino acid sequence is not revealed, can be obtained with relative ease in a desired amount by preparing a recombinant DNA containing a DNA which encodes the enzyme, introducing the recombinant DNA into microorganisms or cells of plants and animals to obtain transformants, and culturing the transformants in nutrient culture media, if only a gene encoding the enzyme were isolated and the nucleotide sequence were decoded. In view of the foregoing, it is urgently required to obtain and reveal a gene encoding a β-fructofuranosidase.

SUMMARY OF THE INVENTION

In view of these circumstances, the first object of the present invention is to provide a polypeptide having a β-fructofuranosidase activity, which can be easily produced in a relatively-large scale by applying the recombinant DNA technology.

The second object of the present invention is to provide a DNA encoding the polypeptide.

The third object of the present invention is to provide a transformant into which the DNA is introduced.

The fourth object of the present invention is to provide a process for producing the polypeptide using the transformant.

The fifth object of the present invention is to provide a method for fructofuranosyl transfer by using the polypeptide.

To overcome the above objects, the present inventors energetically studied and found a polypeptide which has a β-fructofuranosidase activity and the amino acid sequences of SEQ ID NOs:1 and 2 in whole or in part as a partial amino acid sequence and is easily obtainable in a desired amount by the expression of a microbial gene.

The first object of the present invention is solved by a polypeptide which has a β-fructofuranosidase activity and the amino acid sequences of SEQ ID NOs:1 and 2 in whole or in part as a partial amino acid sequence and is obtainable by the expression of a microbial gene.

The second object of the present invention is solved by a DNA encoding the polypeptide.

The third object of the present invention is solved by a transformant into which the DNA is introduced.

The fourth object of the present invention is solved by a process for producing the polypeptide comprising steps of culturing the transformant and collecting the produced polypeptide from the culture.

The fifth object of the present invention is solved by a method for fructofuranosyl transfer comprising a step of reacting a fructofuranosyl donor with a fructofuranosyl acceptor in the presence of the polypeptide.

BRIEF DESCRIPTION OF THE ACCOMPANYING DRAWINGS

DETAILED DESCRIPTION OF THE INVENTION

Figure 1:
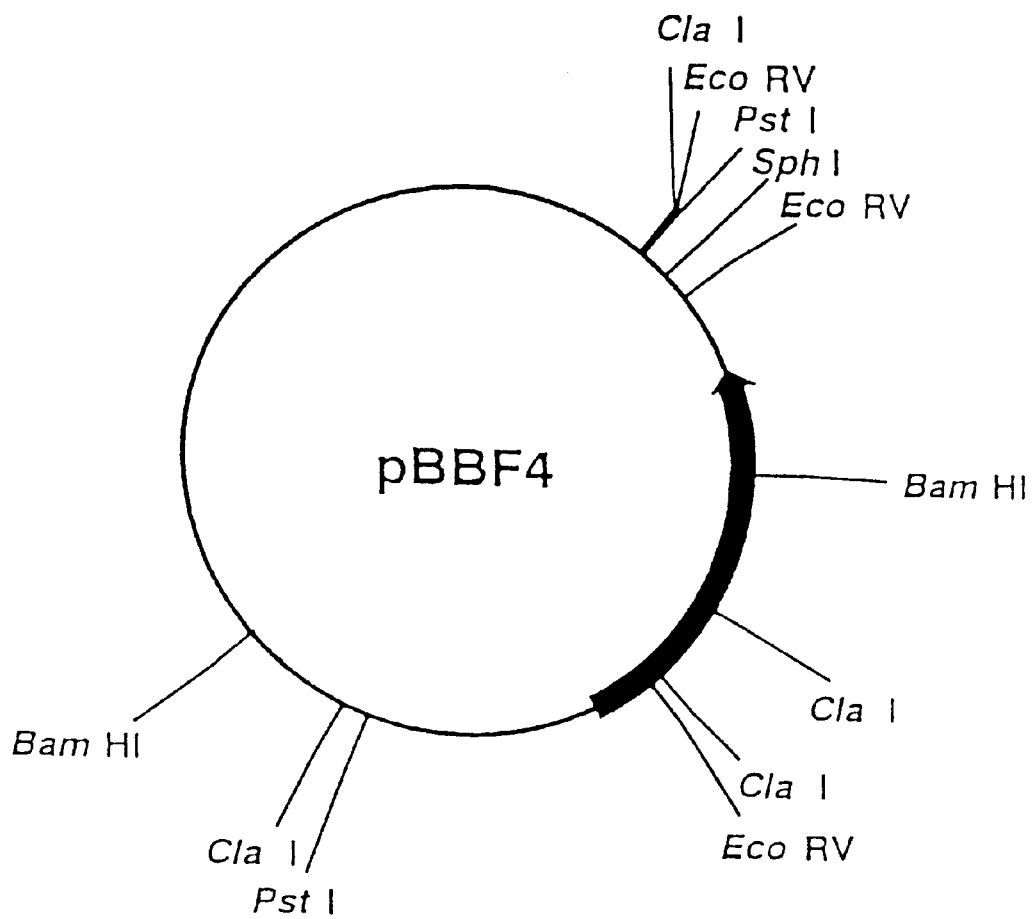
FIG. 1 is a restriction map of the recombinant DNA PGGF4 according to the present invention.

Now explaining the present invention, the wording "polypeptide(s)" as referred to in the present invention means and includes polypeptides in general which are obtainable by the expression of microbial genes and contain the amino acid sequences of SEQ ID NOs:1 and 2 in whole or in part as a partial amino acid sequence. In general, the polypeptide according to the present invention contains an amino acid sequence revealed partly or completely: For example, those which contain the amino acid sequence of SEQ ID NO:3. In addition to a β-fructofuranosidase activity, such a polypeptide catalyzes the fructofuranosyl transfer between appropriate fructofuranosyl donors and fructofuranosyl acceptors and has the following physicochemical properties:

(1) Molecular weight
  About 44,000–54,000 daltons on SDS-PAGE;
(2) Optimum pH
  About 5.5–6.0 when incubated at 40° C. for 10 min;
(3) Optimum temperature
  About 45° C. and about 50° C. in the absence of and in the presence of calcium ion, respectively, when incubated at pH 6.0 for 10 min;
(4) pH Stability
  Stable at a pH of about 5.0–8.0 when incubated at 4° C. for 24 hours; and
(5) Thermal stability
  Stable up to a temperature of about 45° C. when incubated at pH 6.0 for an hour.

To improve the physicochemical properties of polypeptides and the expression level of polypeptides in hosts, the following can be done in this field: (i) One or more amino acids in the amino acid sequences of the polypeptides can be artificially replaced with different amino acids, (ii) one or more amino acids near to the N- and C-termini and/or in the internal sites of the polypeptides can be deleted, and (iii) one or more amino acids can be added to the N-terminus and/or the C-terminus of the polypeptides. Of course, these alterations for amino acid sequences are applicable to the present polypeptide. Depending on the type of hosts and culture conditions for transformants, even in the case of using the same gene, one or more amino acids near to the N- and C-termini of the amino acid sequences of SEQ ID NOs:1 to 3 may be deleted by the modification after the DNA expression by internal enzymes of the hosts. In view of these, the present polypeptide include those which contain amino acid sequences differing from SEQ ID NO:3 as a whole as long as they have a β-fructofuranosidase activity and the amino acid sequences of SEQ ID NOs:1 and 2 in whole or in part as a partial amino acid sequence.

The present polypeptide can be obtained by the expression of a microbial gene, and usually, it can be obtained by using as hosts microorganisms such as *Escherichia coli*, actinomyces, yeasts, and those of the genus Bacillus, and expressing in the hosts genes derived from microorganisms of the genus Bacillus, particularly, a gene of Bacillus sp. V230. Examples of such genes are those which contain the nucleotide sequence of SEQ ID NO:4, more particularly, the one of SEQ ID NO:5 and those which contain DNAs that are complementary to SEQ ID NO:5, and those which contain DNAs obtained by replacing one or more bases in the above nucleotide sequences with different bases with respect to degeneracy of genetic code without altering the amino acid sequences which they encode. To facilitate the gene to express the present polypeptide in hosts, one or more bases in DNAs encoding the present polypeptide can be replaced with different bases, or appropriate enhancers and promoters can be ligated to the DNAs.

Any natural or artificially synthesized gene can be used in the present invention as long as it contains any one of the above DNAs. Natural sources for such a gene include microorganisms of the genus Bacillus such as a Bacillus sp. V230 strain, etc., from which genes that contain the DNAs usable in the present invention can be obtained by inoculating a seed culture of the microorganisms in nutrient culture media, culturing the microorganisms under aerobic conditions for about 1 to 3 days, collecting the proliferated cells from the cultures, treating the cells with cell-wall lysis enzymes or with ultrasonics to extracellularly elute genes containing the desired DNAS. The enzymes can be used in combination with protein-digesting enzymes such as protease, and ultrasonic treatment can be done in the presence of surfactants such as SDS or in combination with freeze-thawing method. The desired DNAs can be collected by applying to the resultant mixtures the methods in general such as phenol extraction, alcohol sedimentation, centrifugation, protease treatment, and ribonuclease treatment. To artificially synthesize the DNAs, they can be chemically synthesized based on the nucleotide sequences of SEQ ID NOs:4 and 5, or by inserting into self-replicable vectors DNAs encoding the amino acid sequence of SEQ ID NO:3 to obtain recombinant DNAs, introducing the recombinant DNAs into appropriate hosts to obtain transformants, culturing the transformants in nutrient culture media, collecting the proliferated transformants from the cultures, and preparing the desired plasmids containing the DNAs from the transformants. Bacillus sp. V230 strain was isolated from a soil in Okayama, Japan, and deposited, on Mar. 24, 1995, in an international depository of microorganisms, i.e., the Fermentation Research Institute, Agency of Industrial Science and Technology, Ibaraki, Japan. The microorganism has been maintained by the institute under the accession number of FERM BP-5054.

The above DNAs are generally introduced into hosts in a recombinant DNA form. Generally, the recombinant DNAs contain the above DNAs and self-replicable vectors, and they can be easily prepared by recombinant DNA technology in general when a material DNA is in hand. Examples of such vectors are plasmid vectors such as pBR322, pUC18, Bluescript II SK(+), pUB110, pTZ4, pC194, pHY300PLK, pHV14, TRp7, TEp7, pBS7, etc.; and phage vectors such as λgt·λC, λgt·λB, ρ11, φ1, φ105, etc. Among these plasmid- and phage-vectors, pBR322, pUC18, Bluescript II SK(+), λgt·λC and λgt·λB are satisfactorily used when the present DNA should be expressed in *Escherichia coli*, while pUB110, pTZ4, pC194, ρ11, φ1and φ105 are satisfactorily used to express the present DNA in microorganisms of the genus Bacillus. The plasmid vectors pHY300PLK, pHV14, TRp7, TEp7 and pBS7 are advantageously used when the recombinant DNAs are allowed to grow in 2 or more hosts.

Methods for inserting the present DNA into vectors include conventional ones used generally in this field. For example, a gene containing the present DNA and a self-replicable vector are first digested by a restriction enzyme and/or ultrasonics, then the resultant DNA fragments and vector fragments are ligated. The ligation of these fragments is facilitated by restriction enzymes which specifically act on nucleotides, particularly, type II restriction enzymes, more particularly, Sau 3AI, Eco RI, Hind III, Bam HI, Sal I, Xba I, Sac I, Pst I, etc. If necessary, these DNA and vector fragments can be annealed before DNA ligases are allowed to act on them in vivo or in vitro to ligate them. The recombinant DNAs thus obtained are replicable without substantial limitation by introducing into appropriate hosts and culturing the transformants in nutrient culture media.

The recombinant DNAs thus obtained can be introduced into appropriate host microorganisms including *Escherichia coli* and those of the genus Bacillus as well as actinomyces and yeasts. In the case of using *Escherichia coli* as a host, the recombinant DNAs can be introduced thereunto by culturing the host in the presence of the recombinant DNAs and calcium ion, while in the case of using a microorganism of the genus Bacillus as a host, the competent cell method and the protoplast method can be used. Desired transformants can be cloned by the colony hybridization method or by culturing a variety of transformants in nutrient culture media containing appropriate fructofuranosyl donors and fructofuranosyl acceptors, and selecting the desired transformants which produce fructofuranosyl-transferred products.

The transformants thus obtained extracellularly produce the present polypeptide when cultured in nutrient culture media. Generally, such culture media include those in general which are supplemented with carbon sources, nitrogen sources and minerals, and if necessary, further supplemented with micronutrients such as amino acids and vitamins. Examples of the carbon sources are saccharides such as starches, starch hydrolysates, glucose, fructose, sucrose and trehalose. Examples of the nitrogen sources are organic- and inorganic-substances containing nitrogen such as ammonia, ammonium salts, urea, nitrates, peptone, yeast extracts, defatted soy beans, corn steep liquors, and beef extracts. Cultures containing the present polypeptide can be obtained by inoculating the transformants into nutrient culture media, and incubating them at temperatures of 20°–65° C. and pHs of 2–9 for about 1–6 days under aerobic conditions such as aeration-agitation conditions. The resultant cultures can be used intact as an enzyme agent, and usually, cells of microorganisms were separated from the cultures by filtration, centrifugation, etc., disrupted by ultrasonics and cell-wall lysis enzymes, filtered and centrifuged to separate the polypeptide from the intact cells and cell debris, followed by purification. Methods for purifying the polypeptide include conventional ones in general: The intact cells and cell debris are eliminated and subjected to one or more methods such as centrifugation, salting out, dialysis, filtration, concentration, separatory sedimentation, ion-exchange chromatography, gel filtration chromatography, isoelectric chromatography, hydrophobic chromatography, reverse-phase chromatography, affinity chromatography, gel electrophoresis and electrofocusing.

As is described above, the present polypeptide having a β-fructofuranosidase activity catalyzes the fructofuranosyl transfer between fructofuranosyl donors and fructofuranosyl acceptors. Therefore, useful fructofuranosyl-transferred products are obtained by reacting appropriate fructofuranosyl donors with fructofuranosyl acceptors in the presence of the polypeptide. Generally, saccharides with β-fructofuranosidic linkages within the molecules such as sucrose, raffinose and erlose can be used as the fructofuranosyl donors, while saccharides free of β-fructofuranosidic linkage within the molecules, for example, reducing sugars such as xylose, xylooligosaccharides, galactose, galactooligosaccharides, lactose, maltose, maltooligosaccharides, isomaltose, and isomaltooligosaccharides; non-reducing saccharides such as trehalose and neotrehalose; sugar alcohols such as sorbitol and maltitol; and alcohols such as glycerol and ethylene glycol. By appropriately combining these compounds, useful fructofuranosyl-transferred saccharides such as xylosylfructoside, erlose, isomaltofructoside, lactosucrose, and fructosyltrehalose can be obtained.

The reaction conditions for fructofuranosyl transfer are generally as follows: A mixture, consisting of one part by weight of a fructofuranosyl acceptor and a fructofuranosyl donor in an amount of about 0.1–10 parts by weight, preferably, about 0.5–5 parts by weight, was dissolved in an aqueous medium to give a concentration of over 10 w/w %, preferably, 20–60 w/w %, and reacted at a temperature of not higher than about 60° C., preferably, at a temperature of about 5°–55° C. and at a pH of about 3.5–8.0, preferably, at a pH of about 4.5–5.5. The amount of the present polypeptide is optionally chosen depending on the reaction conditions, and usually, the reaction terminates within about 0.1–100 hours when used in an amount of about 0.1–50 units/g fructofuranosyl donor, on a dry solid basis (d.s.b.). The reaction mixtures thus obtained contain at least about 5%, usually, at least 10% of fructofuranosyl-transferred products, d.s.b.

The reaction mixtures thus obtained were in a usual manner filtered, centrifuged to remove insoluble substances, purified using activated charcoals and ion exchangers, and concentrated into syrups. If necessary, the syrups can be dried into powders. To increase the content of fructofuranosyl-transferred products, the syrups can be incubated with invertase-defective yeasts to assimilate monosaccharides, treated by heating in the presence of alkalis to decompose reducing saccharides, or either membrane filtered or chromatographed to remove impurities. The column chromatographies using strong-acid cation exchange resins as disclosed in Japanese Patent Laid-Open Nos. 23,799/83 and 72,598/83 can be advantageously used as the methods using chromatography. When applying these column chromatographies, desired amounts of high-purity fructofuranosyl-transferred products can be obtained in a minimum cost and labor. Conventional fixed-bed method, moving-bed method, and pseudo-moving-bed method can be used as the column chromatographies.

The resulting fructofuranosyl-transferred products have a satisfactory taste and sweetness, a moderate viscosity and humectancy, and an effective anticariogenicity, growth-promoting activity for bifid bacteria, and mineral-absorption-promoting activity. Thus, the fructofuranosyl-transferred products, obtained by the present method for fructofuranosyl transfer, can be satisfactorily used to sweeten and improve tastes and textures of food products, cosmetics and pharmaceuticals which require the above properties and activities.

Referring to the examples below, the preferred embodiments according to the present invention will be explained. The techniques per se used therein are conventional ones: Examples of such are disclosed by J. Sambrook et al. in "*Molecular Cloning A Laboratory Manual*", 2nd edition, published by Cold Spring Harbor Laboratory Press, USA (1989).

EXAMPLE 1

Preparation of DNA and Transformant

Example 1-1

Preparation of Purified β-fructofuranosidase

A liquid nutrient culture medium (pH 7.0), consisting of 1.0 w/v % by weight of sucrose, 0.5 w/v % polypeptone, 0.1 w/v % yeast extract, 0.1 w/v % dipotassium hydrogenphosphate, 0.06 w/v % sodium dihydrogenphosphate, dihydrate, 0.05 w/v % magnesium sulfate, heptahydrate, 0.3 w/v % calcium carbonate and water, was prepared. One hundred ml aliquots of the culture medium were distributed to 500-ml flasks, sterilized by autoclaving at 120° C. for 15 min, cooled, inoculated with a seed of Bacillus sp. V230 (FERM BP-5054), and cultured under rotary shaking conditions at 30° C. for 20 hours to obtain a seed culture.

About 7 liters of a fresh preparation of the same liquid nutrient culture medium was placed in a 10-L jar fermenter, sterilized similarly as above, cooled to 30° C., inoculated with one v/v % of the seed culture, and cultured under aeration-agitation conditions at 30° C. for 20 hours. The resultant culture was centrifuged to obtain a 6.3 L supernatant containing 3.6 units/ml of β-fructofuranosidase. To the supernatant was added ammonium sulfate up to give a 80% saturation, allowed to stand at 4° C. overnight, and centrifuged to obtain a precipitate containing β-fructofuranosidase.

The precipitate was dissolved in 10 mM acetate buffer (pH 6.0) containing 5 mM calcium chloride, dialyzed against a fresh preparation of the same acetate buffer for one day, and centrifuged to obtain a 210 ml supernatant. The supernatant was fed to a column packed with 380 ml of "DEAE-TOYOPEARL® 650", a gel for ion-exchange chromatography commercialized by Tosoh Corporation, Tokyo, Japan, which had been previously equilibrated with 10 mM acetate buffer (pH 6.0) containing 5 mM calcium chloride, and fed with a linear gradient buffer of sodium chloride increasing from 0 M to 0.5 M in 10 mM acetate buffer (pH 6.0), followed by collecting fractions eluted at around 0.1 M sodium chloride.

The fractions were pooled, dialyzed against 10 mM acetate buffer (pH 6.0) containing 1 M ammonium sulfate and 5 mM calcium chloride, and centrifuged to obtain a supernatant which was then fed to a column packed with 100 ml of "BUTYL-TOYOPEARL® 650", a hydrophobic gel commercialized by Tosoh Corporation, Tokyo, Japan, which had been equilibrated with 10 mM acetate buffer (pH 6.0) containing 5 mM calcium chloride, and fed with a linear gradient buffer of ammonium sulfate decreasing from 1 M to 0 M in 10 mM acetate buffer (pH 6.0) containing 5 mM calcium chloride, followed by collecting fractions eluted at around 0.1 M ammonium sulfate.

Thereafter, the fractions were pooled, dialyzed against 10 mM acetate buffer (pH 6.0) containing 5 mM calcium chloride, and centrifuged to obtain a supernatant which was then fed to a column packed with 10 ml of "DEAE-TOYOPEARL® 650", a gel commercialized by Tosoh Corporation, Tokyo, Japan, which had been equilibrated with 10 mM acetate buffer (pH 6.0) containing 5 mM calcium chloride, and fractionated similarly as above to obtain 14 mg of a purified β-fructofuranosidase with a specific activity of 205 units/mg protein. When electrophoresed on SDS-PAGE, the purified β-fructofuranosidase was observed as a substantially single protein band with a β-fructofuranosidase activity.

The activity of the present β-fructofuranosidase is assayed as follows: Sucrose as a substrate was dissolved in 20 mM acetate buffer (pH 6.0) containing 5 mM calcium chloride to give a concentration of 0.1 w/v %. To 5 ml of the solution was added 0.2 ml of a test sample, and the mixture was incubated at 40° C. for 10 min, followed by suspending the enzymatic reaction by the addition of 0.2 ml of the Somogyi copper solution and assaying the reducing power of the reaction mixture by the Somogyi-Nelson's method. As a control, a control solution, which was preheated at 100° C. for 10 min to inactivate the enzyme, was treated similarly as above. Under the above reaction conditions, one unit β-fructofuranosidase activity is defined as the amount of enzyme or polypeptide which gives a reducing power equal to that of $2\mu$ mole of glucose per minute.

Example 1-2
Amino Acid Sequence Containing the N-terminus

The amino acid sequence containing the N-terminus of the purified β-fructofuranosidase in Example 1-1 was analyzed on "MODEL 473A", a gas-phase protein sequencer commercialized by Perkin-Elmer Corp., Instrument Div., Norwalk, USA, revealing that it has the amino acid sequence of SEQ ID NO:1.

Example 1-3
Partial Amino Acid Sequence

An adequate amount of a purified β-fructofuranosidase, obtained by the method in Example 1-1, was placed in a container, dialyzed against 10 mM Tris-HCl buffer (pH 9.0) at 4° C. for 18 hours, and admixed with 10 mM Tris-HCl buffer (pH 9.0) to give a protein concentration of about one mg/ml. About one ml of the aqueous solution was placed in a container, admixed with 20 $\mu$g/ml of lysyl endopeptidase, incubated at 30° C. for 60 hours to partially hydrolyze the enzyme. The resultant hydrolysate was applied to "$\mu$BONDAPAK C18", a column for high-performance liquid chromatography commercialized by Japan Millipore Ltd., Tokyo, Japan, which had been equilibrated with 0.1 v/v % trifluoroacetate, followed by feeding to the column a linear gradient of aqueous acetonitrile increasing from 0 v/v % to 40 v/v % in 0.1 v/v % trifluoroacetate at a flow rate of 0.9 ml/min and collecting a fraction containing a peptide fragment eluted about 77 min after initiating the feeding. The fraction was dried in vacuo and dissolved in 0.1 v/v % trifluoroacetate containing 50 v/v % aqueous acetonitrile. Similarly as in Example 1-2, the peptide fragment was analyzed and revealed to have an amino acid sequence of SEQ ID NO:2.

Example 1-4
Preparation of Chromosome DNA

One hundred ml aliquots of a liquid nutrient culture medium (pH 7.0), consisting of one w/v % polypeptone, 0.5 w/v % yeast extract, 0.5 w/v % sodium chloride and water, were distributed to 500-ml flasks, sterilized by autoclaving at 120° C. for 20 min, cooled, inoculated with a seed of Bacillus sp. V230 (FERM BP-5054) strain, and cultured at 27° C. for 24 hours under rotary shaking conditions.

The proliferated cells were separated from the resultant culture by centrifugation, suspended in an adequate amount of TES buffer (pH 8.0), admixed with 0.05 w/v % lysozyme, incubated at 37° C. for 30 min, freezed at −80° C. for an hour, admixed with TSS buffer (pH 9.0), further admixed with a mixture of TES buffer and phenol preheated to 60° C., cooled, and centrifuged to obtain a supernatant. Two-fold volumes of cooled ethanol was added to the supernatant, and the formed sediment containing a chromosome DNA was collected, dissolved in SSC buffer (pH 7.1), admixed with 7.5 $\mu$g ribonuclease and 125 $\mu$g protease, and allowed to react at 37° C. for an hour. The reaction mixture was mixed with a mixture solution of chloroform and isoamyl alcohol to extract the chromosome DNA, and the extract was mixed with cooled ethanol, and allowed to stand to obtain sediment containing a purified chromosome DNA. The sediment was dissolved in SSC buffer (pH 7.1) to give a concentration of about one mg/ml, then freezed at −80° C.

Example 1-5
Preparation of Transformant BBF4

One ml of solution of a purified chromosome DNA, obtained by the method in Example 1-4, was placed in a container, admixed with about 30 units of a restriction enzyme, Sau 3AI, incubated at 37° C. for 20 min to partially hydrolyze the chromosome DNA, and subjected to sucrose gradient centrifugation to obtain a DNA fragment consisting of about 2,000–5,000 base pairs (bp). While a plasmid vector, Bluescript II SK(+), was digested with a restriction enzyme, Bam HI, and 0.1 $\mu$g of the formed vector fragments and the DNA fragments obtained in the above were ligated using "DNA LIGATION KIT", a product of Takara Shuzo Co., Ltd., Otsu, Shiga, Japan. The obtained recombinant DNA was mixed with 30 $\mu$l of "EPICURIAN COLI® XLI-BLUE", a competent cell commercialized by Toyobo Co., Ltd., Tokyo, Japan, allowed to stand under ice-chilled conditions for 30 min, heated to 42° C., admixed with SOC broth, incubated at 37° C. for an 18 hour to introduce the recombinant DNA into *Escherichia coli*.

The resultant transformant was inoculated into an agar plate (pH 7.0) containing 50 $\mu$g/ml of 5-bromo-4-chloro-3-indolyl-p-galactoside, and cultured at 37° C. for 18 hours, followed by fixing about 2,000 colonies formed on the agar plate upon "HYBOND-H+", a nylon film commercialized by Amersham Corp., Div., Amersham International, Arlington Heights, USA. Based on the amino acid sequence of Asp-Tyr-Lys-Glu-Asp-Tyr-Gly-Phe-Ala located at amino acids 5-13 in SEQ ID NO:3, an oligonucleotide with a nucleotide sequence of 5'-GAYTAYAARGARGAYTAYGGNTTYGC-3' (SEQ ID NO:6 was chemically synthesized, and labelled with $^{32}$p The resultant as a probe was hybridized with the colonies of transformants fixed on the nylon film, followed by selecting a transformant which showed a strong hybridization and named "BBF4".

The transformant BBF4 was inoculated into L-broth (pH 7.0) containing 100 μg/ml ampicillin and cultured at 37° C. for 24 hours under rotary shaking conditions. The proliferated cells were collected by centrifugation from the culture, treated with conventional alkali-treatment to extract extracellularly the recombinant DNA which was then purified and analyzed in a conventional manner, revealing that the recombinant DNA contained in the transformant BBF4, i.e., "pBBF4", consisted of about 6,300 bp and had the restriction sites as shown in FIG. 1. As is evident from FIG. 1, in the recombinant pBBF4, the DNA consisting of 1,365 bp which encodes the present polypeptide is linked to the downstream of a restriction site by a restriction enzyme, Eco RV.

Example 1-6
Decoding of Nucleotide Sequence

One μg of the recombinant DNA pBBF4 in Example 1-5 was weighed and placed in a container, then mixed with 0.02 μg of a sequencing primer and 9.5 μl of a premix solution used in "ABI PRISM™ READY REACTION TERMINATOR CYCLE SEQUENCING KIT" commercialized by Applied Biosystems, Inc., Foster City, USA, and volumed up to give a total volume of 20 μl by the addition of an adequate amount of water. An adequate amount of mineral oil was overlaid on the mixture, and the resultant mixture was incubated at 96° C. for 30 sec, 50° C. for 15 sec, and 60° C. for 4 min using "MODEL PJ200" commercialized by Perkin-Elmer Corp., Norwalk, USA, and the above serial incubations were repeated 25 times to obtain a reaction product containing a complementary DNA (cDNA). Thereafter, the reaction product was mixed with 2.5 μl of 0.5 M aqueous salt solution containing 5 w/v % cetyltrimethylammonium bromide for sedimentation, and the sediment was purified by conventional ethanol method and dried in vacuo. The powdery product thus obtained was dissolved by admixing with one μl of 50 mM EDTA and 5 μl formamide, and the solution was incubated at 90° C. for 2 min and instantly cooled.

The resulting product was weighed in an appropriate amount, placed on 6 w/v polyacrylamide gel set to "MODEL 373", a DNA sequencing system commercialized by Applied Biosystems, Inc., Foster City, USA, electrophoresed for separation and analyzed, revealing that the cDNA contained the nucleotide sequence of SEQ ID NO:5. An amino acid sequence estimable from the nucleotide sequence was SEQ ID NO:3. Comparison of the amino acid sequence with the partial amino acid sequences of SEQ ID NOs:1 and 2 revealed that SEQ ID NO:1 and SEQ ID NO:2 coincided with the amino acids 1–21 and those 201–212 in SEQ ID NO:3, respectively. The data indicates that the present polypeptide contains the amino acid sequence of SEQ ID NO:3, and a polypeptide from Bacillus sp. V230 strain has the amino acid sequence of SEQ ID NO:4, more particularly, it is encoded, by the DNA in SEQ ID NO:5. It can be estimated that the nucleotide sequence of bases 361–456 in SEQ ID NO:5 is a common signal peptide region, found in secretory enzymes in general.

EXAMPLE 2

Preparation of Polypeptide by Transformant and Physicochemical Properties Thereof Example 2-1
Preparation of Polypeptide by Transformant Into 500-ml flasks were distributed 100 ml aliquots of a liquid nutrient culture medium consisting of 1.0 w/v % sucrose, 0.5 w/v % polypeptone, 0.1 w/v % yeast extract, 0.1 w/v % dipotassium hydrogenphosphate, 0.06 w/v % sodium dihydrogenphosphate, dihydrate, 0.05 w/v % magnesium sulfate, heptahydrate, 0.3 w/v % calcium carbonate, and water. The flasks were autoclaved at 120° C. for 15 min for sterilization, cooled, adjusted to pH 7.0 and mixed with 50 μg/ml ampicillin, followed by inoculating thereunto the transformant BBF4 in Example 1-5 and incubating the mixture at 37° C. for 20 hours under rotary conditions to obtain a seed culture.

An about 7 L of a fresh preparation of the same liquid nutrient culture medium was placed in a 10-L jar fermenter, sterilized similarly as above, cooled to 37° C., adjusted the pH, admixed with ampicillin, inoculated with one v/v % of the seed culture, and cultured for 20 hours under aeration-agitation conditions. The resulting culture was treated with ultrasonics to disrupt the proliferated cells and centrifuged to remove impurities, and the supernatant was mixed with ammonium sulfate to give a saturation degree of 70 w/v %, allowed to stand at 4° C. for 24 hours, and centrifuged to collect sediment. The sediment was dissolved in 10 mM phosphate buffer (pH 7.0), and the solution was dialyzed against 10 mM phosphate buffer at 4° C. for 24 hours. The dialyzed inner solution was assayed for β-fructofuranosidase activity, revealing that it produced about 8 units polypeptide per L of the culture. Purification of the resulting crude polypeptide by the method in Example 1-1 yielded an about 8 mg polypeptide with a specific activity of 205 units/mg protein per L of the culture.

As a control, an *Escherichia coli* XLI-Blue strain or a Bacillus sp. V230 strain was similarly cultured in a fresh preparation of the same liquid nutrient culture medium free of ampicillin and treated except that the culturing temperature for the Bacillus sp. V230 strain was set to 30° C. Assay for activity of the resulting supernatant revealed that the Bacillus sp. V230 strain produced an about 3.6 units β-fructofuranosidase, the level of which was significantly lower than that of the transformant BBF4. The *Escherichia coli* XLI-Blue strain used as the host produced no β-fructofuranosidase.

Example 2-2
Physicochemical Properties of Polypeptide

Example 2-2(a)
Action

An aqueous solution, containing as a substrate sucrose, raffinose, erlose, stachyose, lactosucrose, xylosylfructoside, maltose, cellobiose, lactose, inulin or levan in a concentration of 2 w/v %, was mixed with 2 units/g substrate, d.s.b., of a polypeptide obtained by the method in Example 2-1 and reacted at 40° C. and pH 5.5 for 24 hours.

An adequate amount of each reaction mixture was spotted on "KIESELGEL 60", an aluminum plate for thin layer chromatography (TLC) commercialized by Merck & Co., Inc., Rahway, USA, developed at ambient temperature using a developing solvent system of 1-butanol, pyridine and water (=7:3:1 by volume), and dried. When the reaction mixture contained fructose, the plate was colored by spraying 0.5 N phosphate solution containing 0.2 w/v % naphthoresorcinol, and heated at 110° C. for 5 min, while the plate was colored by spraying a mixture solution of 20 w/v % sulfuric acid in methanol and heated at 110° C. for 10 min. As a result, it was revealed that the polypeptide used in this experiment acted on sucrose, raffinose, erlose, stachyose, lactosucrose and xylosylfructoside to release fructose while exerting a β-fructofuranosidase activity, but did not substantially act on maltose, cellobiose, lactose, inulin and levan.

Using as fructofuranosyl acceptors the monosaccharides, oligosaccharides and alcohols in Table 1, the specificity of fructofuranosyl transfer by the present polypeptide was studied: Any one of fructofuranosyl acceptors in Table 1 and sucrose as a fructofuranosyl donor were mixed in an equal amount by weight, and the mixture was dissolved in water into a 10 w/v % aqueous solution which was then mixed with 2 units/g sucrose, d.s.b., of a polypeptide obtained by the method in Example 2-1, and reacted at 40° C. and pH 5.5 for 24 hours. Thereafter, the reaction mixture was separated by TCL similarly as above, and the plate was colored by spraying 0.5 N phosphate solution containing 0.2 w/v % naphthoresorcinol, and the plate was heated at 110° C. for 5 min to color and detect fructofuranosyl-transferred products. The results were in Table 1.

TABLE 1

| Fructofuranosyl acceptor | Formation of fructofuranosyl-transferred product |
| --- | --- |
| D-Xylose | ++ |
| D-Galactose | ++ |
| D-Mannose | + |
| D-Fructose | + |
| L-Sorbose | + |
| L-Arabinose | + |
| L-Rhamnose | + |
| Maltose | ++ |
| Isomaltose | ++ |
| Kojibiose | + |
| Trehalose | ++ |
| Neotrehalose | + |
| Cellobiose | ++ |
| Maltotriose | ++ |
| Panose | ++ |
| Lactose | ++ |
| Turanose | + |
| Palatinose | + |
| Melibiose | ++ |
| Raffinose | + |
| D-Xylitol | ++ |
| D-Sorbitol | ++ |
| Maltitol | ++ |
| Glycerol | ++ |
| Methanol | + |
| Ethanol | + |
| Ethylene glycol | ++ |
| 1-Butanol | – |
| 2-Butanol | – |
| 1-Propanol | – |
| 2-Propanol | – |

Note:
Standards for judgement
Compared with a reaction mixture of sucrose, "–" means unchanged; "+", the size and color of a spot for fructofuranosyl acceptor reduced slightly, and a spot for fructofuranosyl-transferred product was slightly detected; "++", the size and color of a spot for fructofuranosyl acceptor more reduced and a spot for fructofuranosyl-transferred product was clearly observed.

As is evident from the results in Table 1, the present polypeptide catalyzes the transfer of fructofuranosyl residue from sucrose as a fructofuranosyl donor to D-xylose, D-galactose, maltose, isomaltose, cellobiose, maltotriose, panose, lactose, melibiose and trehalose as fructofuranosyl acceptors so as to form fructofuranosyl-transferred products corresponding to the fructofuranosyl acceptors. In addition to the above saccharides, the present polypeptide acts on sugar alcohols such as D-xylitol, D-sorbitol and maltitol, and alcohols such as glycerol and ethylene glycol to form their corresponding fructofuranosyl-transferred products.

Example 2-2(b)

Molecular Weight

The polypeptide in Example 2-1 was subjected to an electrophoresis using 10 w/v % SDS-polyacrylamide gel, and the molecular weight was determined by comparing the mobility of the polypeptide with those of molecular marker proteins electrophoresed simultaneously, revealing that it was 44,000–54,000 daltons. The molecular marker proteins were rabbit muscular phosphorylase B (MW 97,400 daltons), calf serum albumin (MW 66,200 daltons), ovalbumin (MW 45,000 daltons), calf carbonic anhydrase (MW 31,000 daltons), soybean trypsin inhibitor (MW 21,500 daltons), and egg albumin (MW 14,400 daltons).

Example 2-2(c)

Optimum pH

Figure 2:
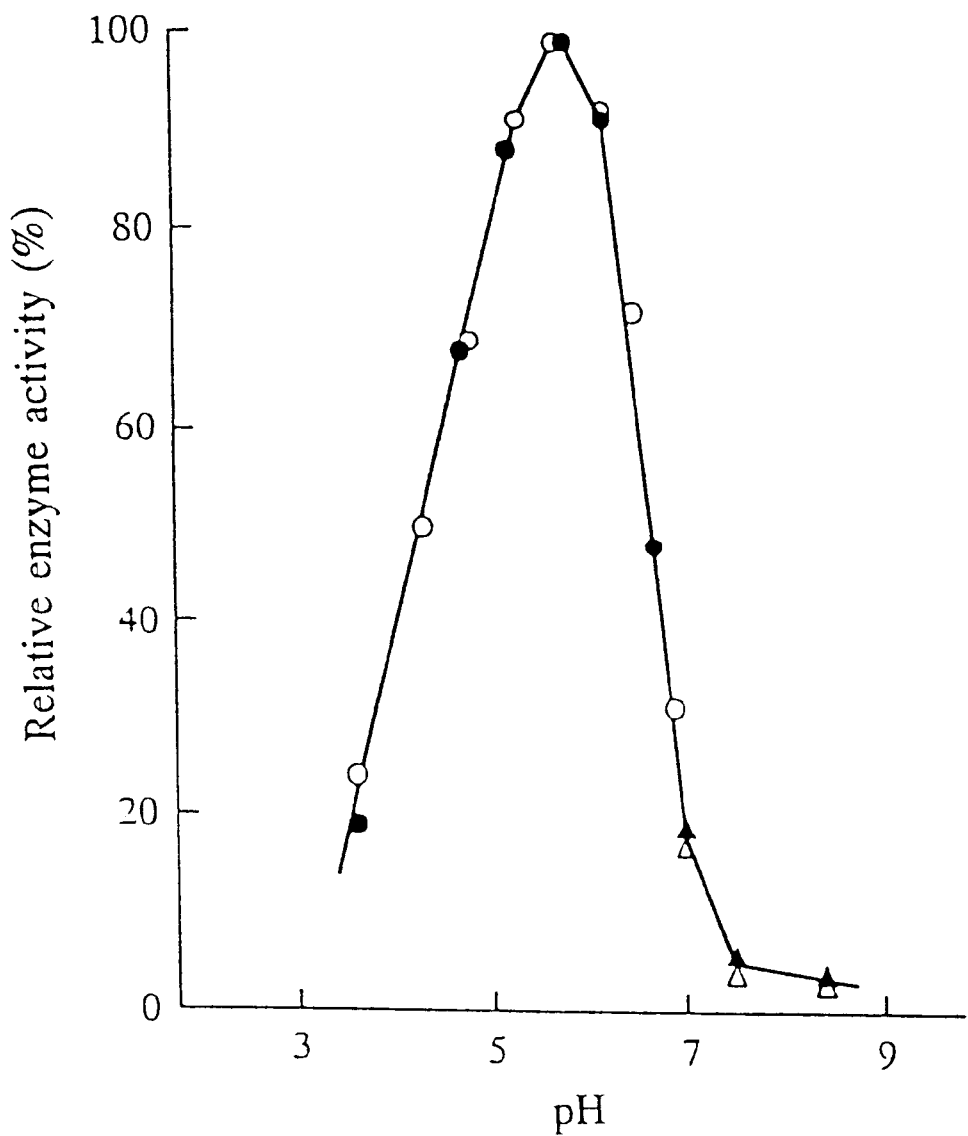
FIG. 2 is a figure of the optimum pH of the polypeptide in Example of the present invention.

The polypeptide in Example 2-1 was in a conventional manner incubated at 40° C. for 10 min in 20 mM buffers with different pHs, revealing that it showed an optimum pH of about 5.5–6.0 as shown in FIG. 2.

Example 2-2(d)

Optimum Temperature

Figure 3:
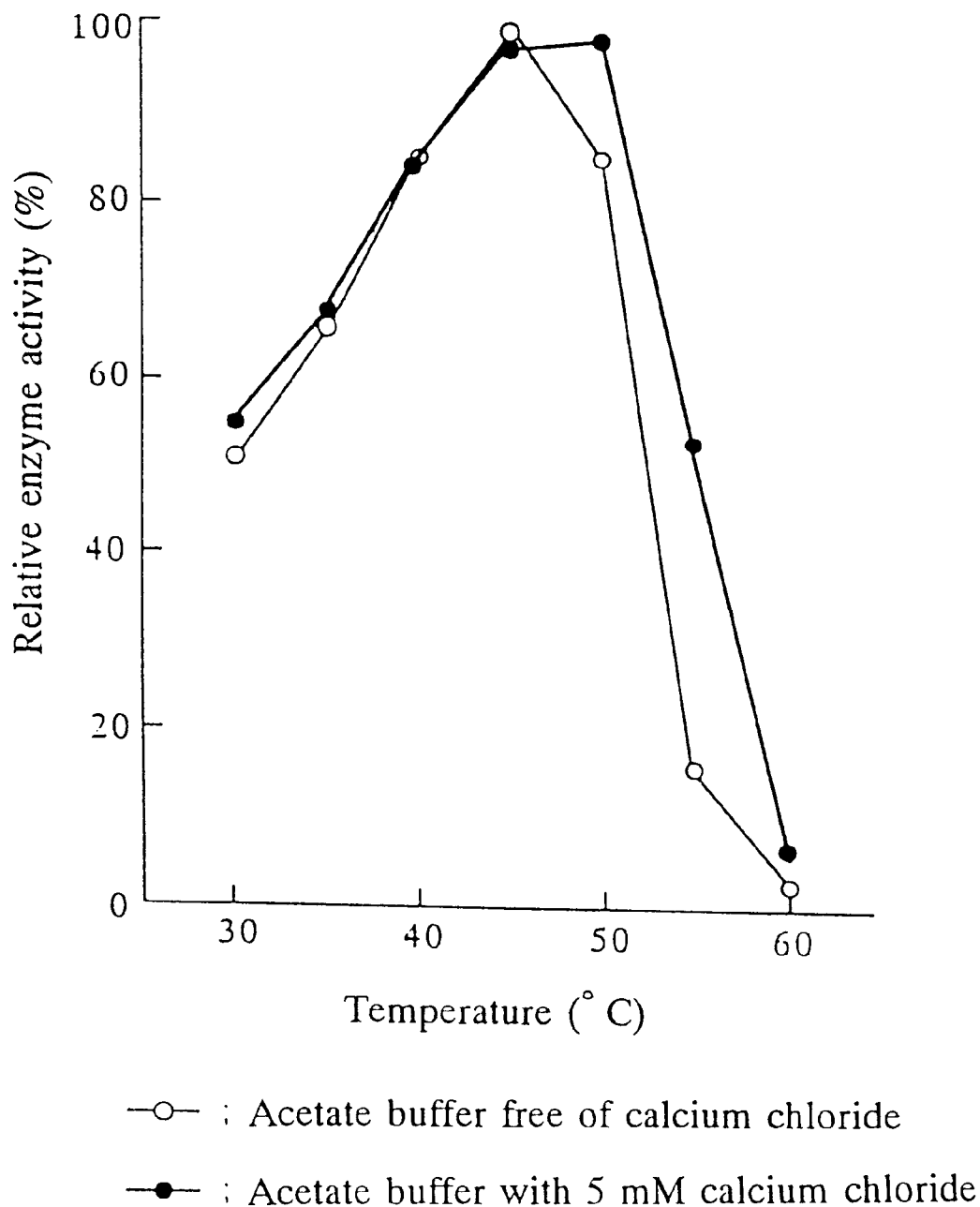
FIG. 3 is a figure of the optimum temperature of the polypeptide in Example of the present invention.

The polypeptide in Example 2-1 was in a conventional manner incubated for 10 min in 20 mM acetate buffer (pH 6.0), revealing that it showed an optimum temperature of about 50° C. and 45° C. in the presence of or in the absence of 5 mM calcium ion as shown in FIG. 3.

Example 2-2(e)

pH Stability

Figure 4:
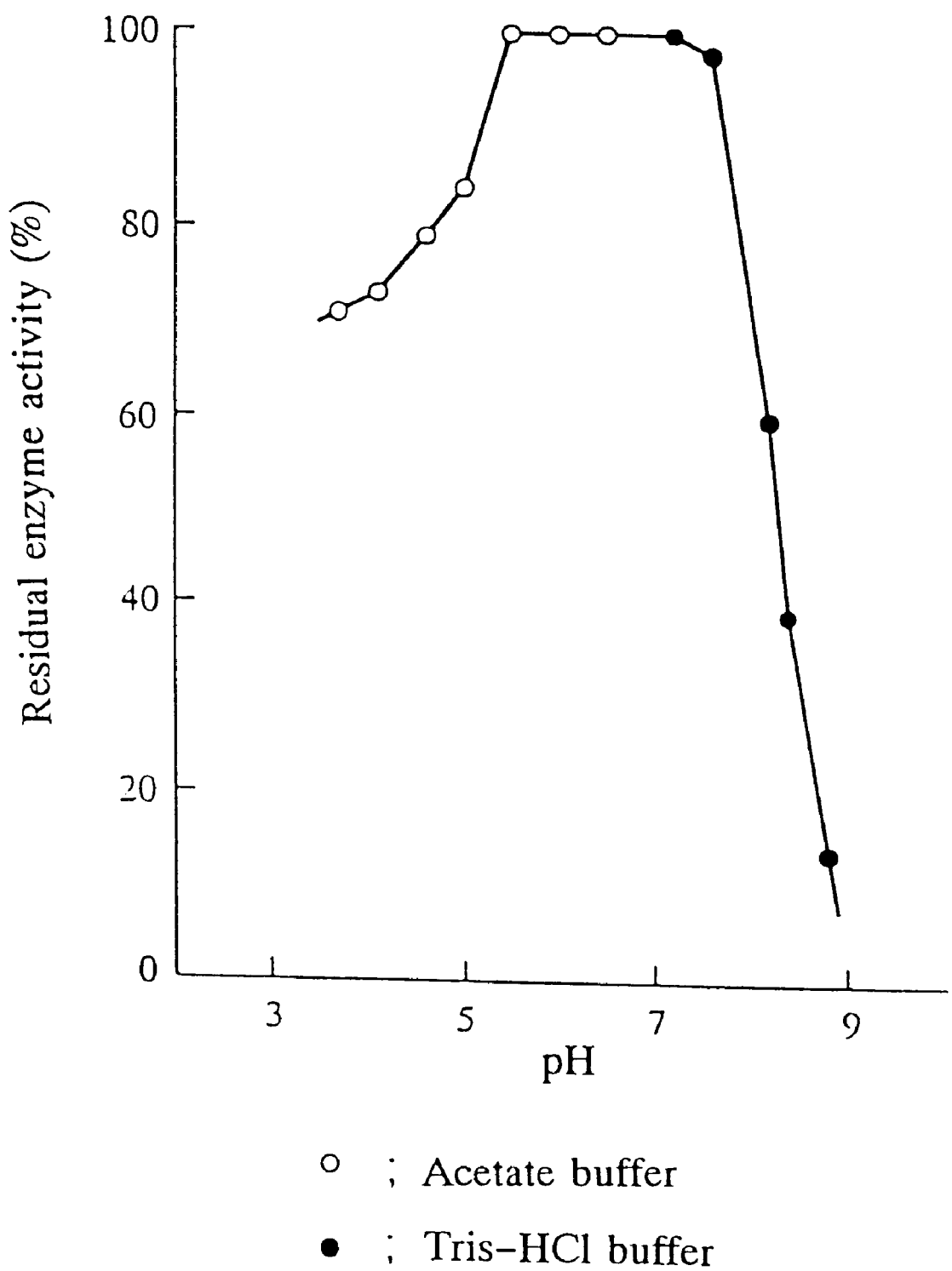
FIG. 4 is a figure of the pH stability of the polypeptide in Example of the present invention.

The polypeptide in Example 2-1 was in a conventional manner incubated at 4° C. for 24 hours in 100 mM buffers with different pHs, revealing that it was stable at pHs from about 5.0 to about 8.0 as shown in FIG. 4.

Example 2-2(f)

Thermal Stability

Figure 5:
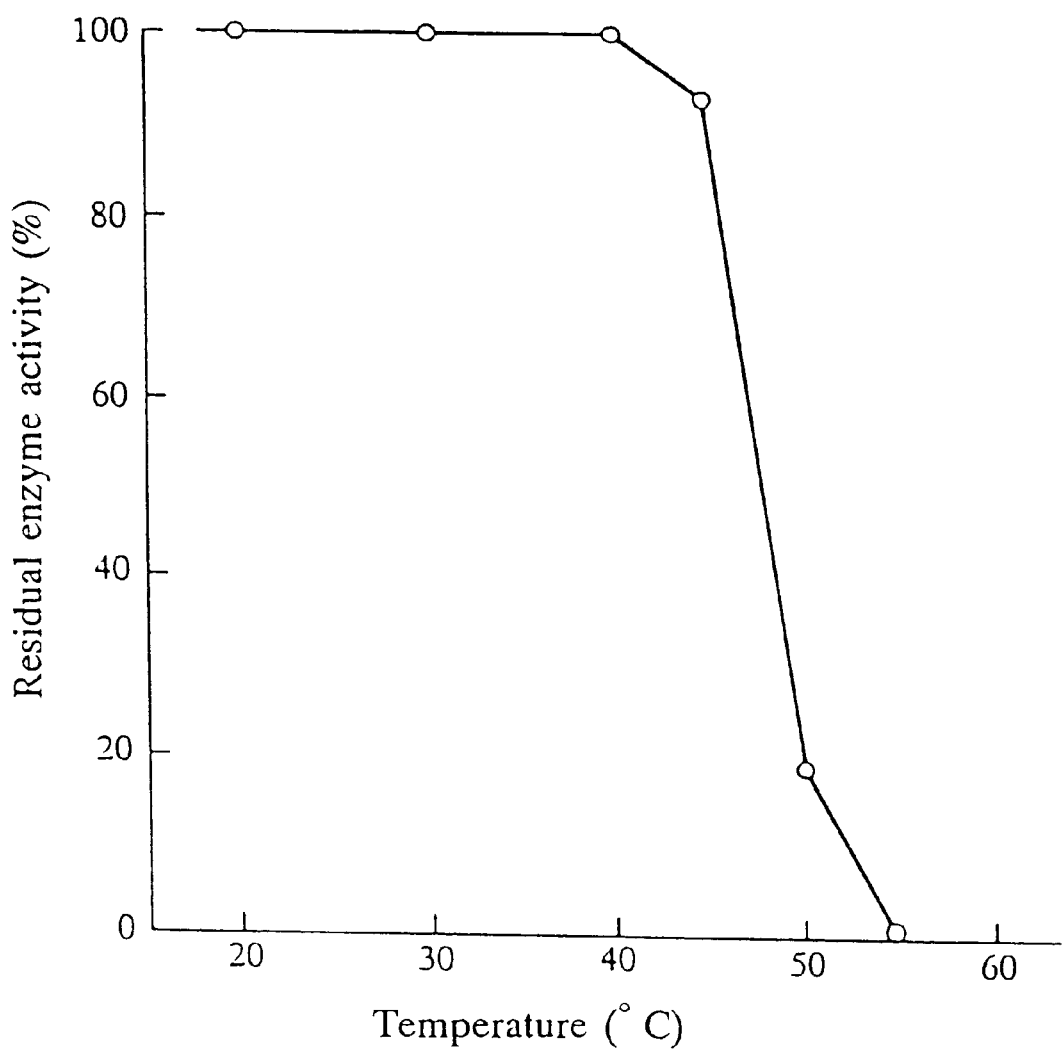
FIG. 5 is a figure of the thermal stability of the polypeptide in Example of the present invention.

The polypeptide in Example 2-1 was in a conventional manner incubated for 60 min in 50 mM acetate buffer (pH 6.0), revealing that it was stable up to a temperature of about 45° C. as shown in FIG. 5.

EXAMPLE 3

Preparation of Polypeptide by Transformant

Example 3-1
Preparation of Transformant BB5

The recombinant DNA pBBF4 in Example 1-5 was cleaved with a restriction enzyme, Pst I, and the cleaved sites were blunted using "DNA BLUNTING KIT" commercialized by Takara Shuzo Co., Ltd., Otsu, Shiga, Japan, and subjected to agarose gel electrophoresis in a conventional manner to obtain a DNA fragment of about 2,800 bp which contained a nucleotide sequence encoding the polypeptide. The DNA fragment was ligated with "pHY300PLK", a plasmid vector commercialized by Toyobo Co., Ltd., Tokyo, Japan, using "DNA LIGATION KIT" commercialized by Takara Shuzo Co., Ltd., Otsu, Shiga, Japan. The resulting recombinant DNA was added to a *Bacillus subtilis* ISW1214 strain, which had been prepared into a protoplast according to the method reported by P. Schaeffer et al. in "*Proceedings of the National Academy of Sciences of the United States of America*", Vol.73, pp.2,151–2,155 (1976), and the strain was transformed according to the method reported by J. Sekiguchi in "*Agricultural and Biological Chemistry*", Vol.46, pp.1,617–1,621 (1982). The transformant thus obtained was named "BBF5".

Figure 6:
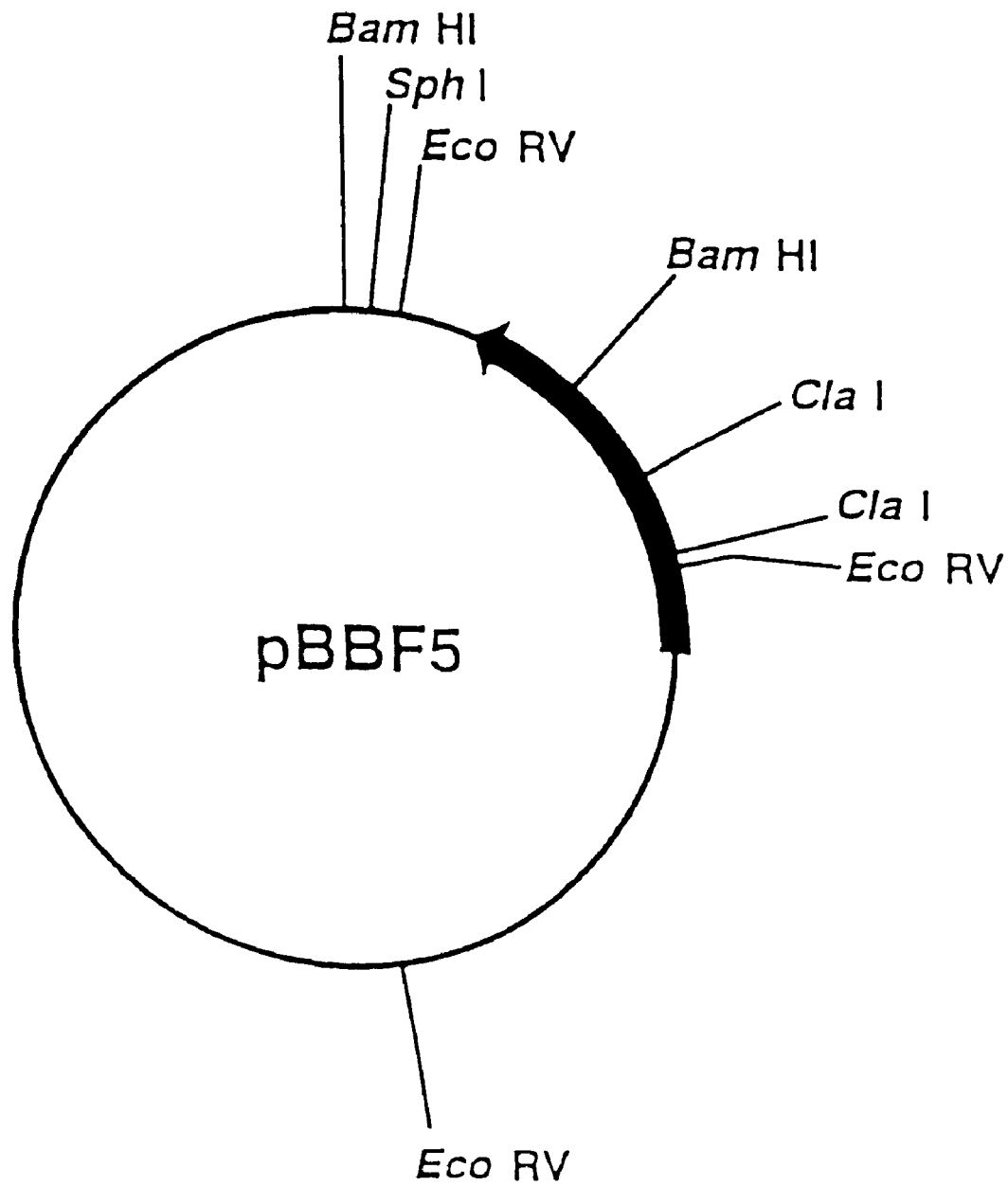
FIG. 6 is a restriction map of the recombinant DNA pBBF5 according to the present invention.

The transformant BBF5 was inoculated into L-broth (pH 7.0) containing 10 µg/ml tetracycline and incubated at 30° C. for 24 hours under rotary shaking conditions. Similarly as in Example 1-4, a desired recombinant DNA was extracted, purified and analyzed, revealing that the recombinant DNA, which contained in the transformant BBF5, consisted of about 7,700 bp and had the restriction sites as shown in FIG. 6.

Example 3-2

Production of Polypeptide by Transformant

One hundred ml aliquots of a liquid nutrient culture medium, consisting of 5.0 w/v % sucrose, 1.0 w/v % polypeptone, 0.1 w/v % yeast extract, 0.1 w/v % dipotassium hydrogenphosphate, 0.06 w/v % sodium dihydrogenphosphate, dihydrate, 0.05 w/v % magnesium sulfate, heptahydrate, 0.3 w/v % calcium carbonate, and water, were distributed to 500-ml flasks which were then sterilized by autoclaving at 120° C. for 15 min, cooled, adjusted to pH 7.0, and admixed with 10 µg/ml tetracycline. Into each flask containing the liquid nutrient culture medium was inoculated the transformant BBF5 in Example 3-1 and incubated at 30° C. for 24 hours under rotary shaking conditions to obtain a seed culture.

About 19 L of a fresh preparation of the same liquid nutrient culture medium as used in the above was placed in a 30-L fermenter, sterilized similarly as above, cooled to 30° C., adjusted the pH, admixed with tetracycline, inoculated with one v/v % of the seed culture, and cultured for 24 hours under aeration-agitation conditions. Most of the polypeptide produced by the transformant BBF5 was found in the culture supernatant with a β-fructofuranosidase activity of 45 units/ml. The culture supernatant was filtered using an MF membrane and concentrated with a UF membrane to obtain an 820 ml aqueous solution containing about 800 units/ml of the present polypeptide.

Similarly as in Example 1-1, the polypeptide was purified and studied on the physicochemical properties using the method in Example 2-2, revealing that it had the same physicochemical properties as those of the one in Example 2-1.

EXAMPLE 4

Fructofuranosyl Transfer to Lactose

An aqueous solution, containing 20 w/w % sucrose as a fructofuranosyl donor and lactose as a fructofuranosyl acceptor, was adjusted to pH 5.5, admixed with one unit/g sucrose, d.s.b., of a crude polypeptide obtained by the method in Example 2-1, and reacted at 55° C. for 16 hours. The reaction mixture was heated at 90° C. for 30 min to inactivate the polypeptide, cooled, and in a conventional manner, decolored with an activated charcoal, filtered, desalted and purified using ion exchangers, and concentrated to obtain a 75 w/w % syrupy product in a yield of 95% to the material, d.s.b.

The product, containing 37% lactosucrose, d.s.b., has a satisfactory taste and sweetness, and an adequate humectancy, and can be arbitrarily used in food products, cosmetics and pharmaceuticals as a sweetener, taste-improving agent, stabilizer, growth-promoting agent for bifid bacteria, and mineral absorption-promoting agent.

EXAMPLE 5

Fructofuranosyl Transfer to Lactose

An aqueous solution, containing 22 w/w % sucrose as a fructofuranosyl donor and 18 w/w % lactose as a fructofuranosyl acceptor, was adjusted to pH 6.0, admixed with one unit/g sucrose, d.s.b., of a crude polypeptide obtained by the method in Example 1-1 and 5 w/w % by wet weight of invertase defective yeasts, and enzymatically reacted at 35° C. for 20 hours while keeping the pH in the range of 6–7 by the addition of 1N sodium hydroxide solution. The reaction mixture was heated at 90° C. for 30 min to inactivate the polypeptide, cooled, and in a conventional manner, decolored with an activated charcoal, desalted and purified using ion exchangers, concentrated, dried in vacuo, and pulverized to obtain a powdery product in a yield of 70% to the material, d.s.b.

The product, containing 65% lactosucrose, d.s.b., has a satisfactory taste and sweetness, and an adequate humectancy, and can be arbitrarily used in food products, cosmetics and pharmaceuticals as a sweetener, taste-improving agent, stabilizer, growth-promoting agent for bifid bacteria, and mineral absorption-promoting agent.

EXAMPLE 6

Fructofuranosyl Transfer to Maltose

An aqueous solution, containing sucrose as a fructofuranosyl donor and 20 w/w % maltose as a fructofuranosyl acceptor, was adjusted to pH 5.5, admixed with one unit/g sucrose, d.s.b., of a crude polypeptide obtained by the method in Example 2-1, and enzymatically reacted at 50° C. for 24 hours. The reaction mixture was heated at 90° C. for 30 min to inactivate the polypeptide, cooled, and in a conventional manner, decolored with an activated charcoal, desalted and purified using ion exchangers, concentrated, dried in vacuo, and pulverized to obtain a 75 w/w % syrupy product in a yield of 95% to the material, d.s.b. The syrupy product contained about 28% erlose, d.s.b.

The syrupy product was concentrated up to give a concentration of 45 w/w % and subjected to column chromatography using "DOWEX 50W X4 (Ca-form)", an alkaline metal strong-acid cation exchanger commercialized by Dow Chemical Co., Midland, Mich., USA, to increase the erlose content: The exchanger was injected into 4 jacketed stainless-steel columns, having an inner diameter of 5.4 cm, and the columns were cascaded in series to give a total gel-bed depth of 20 m, fed with 5 v/v % of the syrupy product to the exchanger while keeping the inner column temperature at 40° C., and fed with water heated to 40° C. at an SV (space velocity) 0.2 to effect fractionation. Thereafter, high-erlose content fractions were collected, and in a conventional manner, purified, concentrated, dried in vacuo, and pulverized to obtain a powdery product containing 84% erlose, d.s.b., in a yield of 25% to the material, d.s.b.

The product has a satisfactory taste and sweetness, and an adequate humectancy, and can be arbitrarily used in food products, cosmetics and pharmaceuticals as a sweetener, taste-improving agent, stabilizer, growth-promoting agent for bifid bacteria, and mineral absorption-promoting agent. Because the product has a relatively-low reducibility, satisfactory taste and sweetness, adequate humectancy, and relatively-low cariogenicity, it can be arbitrarily used in food products, cosmetics and pharmaceuticals as a sweetener, taste-improving agent, stabilizer, growth-promoting agent for bifid bacteria, and mineral absorption-promoting agent.

EXAMPLE 7

Fructofuranosyl Transfer to Xylose

An aqueous solution, containing 30 w/w % sucrose as a fructofuranosyl donor and 15 w/w % xylose as a fructofuranosyl acceptor, was adjusted to pH 5.5, admixed with 0.5 unit/g sucrose, d.s.b., of a crude polypeptide obtained by the method in Example 1–2, and enzymatically reacted at 50° C. for 40 hours. The reaction mixture was heated at 90° C. for 30 min to inactivate the polypeptide, cooled, and in a conventional manner, decolored with an activated charcoal, desalted and purified using ion exchangers, and concentrated to obtain a 75 w/w % syrupy product in a yield of 95% to the material, d.s.b.

Since the product contains 35% xylosylfructoside, d.s.b., and has a satisfactory taste and sweetness, adequate humectancy, and relatively-low cariogenicity, it can be arbitrarily used in food products, cosmetics and pharmaceuticals as a sweetener, taste-improving agent, stabilizer, growth-promoting agent for bifid bacteria, and mineral absorption-promoting agent.

EXAMPLE 8

Fructofuranosyl Transfer to Xylose

An aqueous solution, containing 30 w/w % sucrose as a fructofuranosyl donor and 15 w/w % xylose as a fructofuranosyl acceptor, was adjusted to pH 6.0, admixed with 0.5 unit/g sucrose, d.s.b., of a crude polypeptide obtained by the method in Example 3-1, and enzymatically reacted at 50° C. for 40 hours. The reaction mixture was heated at over 100° C. while keeping the pH to 10 or higher by the addition of sodium hydroxide, cooled, and in a conventional manner, decolored with an activated charcoal, desalted and purified using ion exchangers, and concentrated to obtain a 75 w/w % syrupy product in a yield of 55% to the material, d.s.b.

Since the product contains 60% xylosylfructoside, d.s.b., and has a satisfactory taste and sweetness, adequate humectancy, and relatively-low cariogenicity, it can be arbitrarily used in food products, cosmetics and pharmaceuticals as a sweetener, taste-improving agent, stabilizer, growth-promoting agent for bifid bacteria, and mineral absorption-promoting agent.

EXAMPLE 9

Fructofuranosyl Transfer to Trehalose

An aqueous solution, containing 14 w/w % raffinose as a fructofuranosyl donor and 10 w/w % trehalose as a fructofuranosyl acceptor, was adjusted to pH 5.5, admixed with 0.4 unit/g sucrose, d.s.b., of a crude polypeptide obtained by the method in Example 2-1, and enzymatically reacted at 50° C. for 40 hours. The reaction mixture was heated at 90° C. for 30 min to inactivate the polypeptide, cooled, and in a conventional manner, decolored with an activated charcoal, desalted and purified using ion exchangers, concentrated, dried in vacuo, and pulverized to obtain a powdery product in a yield of 95% to the material, d.s.b.

The product, containing 20% fructofuranosyl trehalose, d.s.b., has a satisfactory taste and sweetness and an adequate humectancy, and can be arbitrarily used in food products, cosmetics and pharmaceuticals as a sweetener, taste-improving agent, stabilizer, growth-promoting agent for bifid bacteria, and mineral absorption-promoting agent.

As is described above, the present invention provides a polypeptide with a β-fructofuranosidase activity, which can be easily and industrially produced by applying recombinant DNA technology. The present polypeptide is one with a revealed amino acid sequence in whole or in part and can be arbitrarily used in the production of fructofuranosyl-transferred products directed to use in food products, cosmetics and pharmaceuticals. The polypeptide with such useful properties can be easily produced in a desired amount by the present method using transformants.

Therefore, the present invention with these useful and satisfactory effects and activities is a significant invention that greatly contributes to the field.

While there has been described what is at present considered to be the preferred embodiments of the invention, it will be understood the various modifications may be made therein, and it is intended to cover in the appended claims all such modifications as fall within the true spirit and scope of the invention.

---

What is claimed is:

1. A method for fructofuranosyl transfer comprising reacting a fructofuranosyl donor with a fructofuranosyl acceptor in the presence of a polypeptide to transfer a fructofuranosyl residue from said fructofuranosyl donor to said fructofuranosyl acceptor, said polypeptide having β-fructofuranosidase activity, said polypeptide being obtainable by using a microorganism as a host and by expressing in said host a gene derived from a microorganism of the genus Bacillus, containing the amino acid sequences of SEQ ID NOs:1 and 2 as partial amino acid sequences, and having the following physicochemical properties:

(1) Molecular weight about 44,000 to 54,000 daltons on sodium dodecyl sulfate polyacrylamide gel electrophoresis (SDS-PAGE);
   (2) Optimum pH about 5.5–6.0 when incubated at 10° C. for 10 min;
   (3) Optimum temperature about 45° C. and about 50° C. in the absence of and in the presence of calcium ion, respectively, when incubated at pH 6.0 for 10 min;
   (4) pH stability stable at a pH of about 5.0–8.0 when incubated at 4° C. for 24 hours; and
   (5) thermal stability stable up to a temperature of about 45° C. when incubated at pH 6.0 for an hour.

2. The method of claim 1, wherein said fructofuranosyl donor is a member selected from the group consisting of sucrose, raffinose, and erlose.

3. The method of claim 1, wherein said fructofuranosyl acceptor is a member selected from the group consisting of alcohols, sugar alcohols, and saccharides free of β-fructofuranosidic linkage within the molecules.

4. The method of claim 1, wherein a reaction product is a member selected from the group consisting of xylosylfructoside, erlose, isomaltosylfructoside, lactosucrose, and fructosyltrehalose.

5. The method of claim 1, wherein 0.1–10 parts by weight of a fructofuranosyl acceptor is reacted with one part by weight of a fructofuranosyl donor at a pH of 3.5–8.0 and at a temperature of no more than 60° C.

* * * * *